US007985839B2

(12) United States Patent
Turecek et al.

(10) Patent No.: US 7,985,839 B2
(45) Date of Patent: *Jul. 26, 2011

(54) FACTOR VIII POLYMER CONJUGATES

(75) Inventors: Peter Turecek, Klosterneuburg (AT); Juergen Siekmann, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/684,482

(22) Filed: Jan. 8, 2010

(65) Prior Publication Data

US 2010/0113364 A1    May 6, 2010

Related U.S. Application Data

(60) Division of application No. 12/184,567, filed on Aug. 1, 2008, now Pat. No. 7,645,860, which is a continuation-in-part of application No. 11/729,625, filed on Mar. 29, 2007, now Pat. No. 7,683,158.

(60) Provisional application No. 60/787,968, filed on Mar. 31, 2006, provisional application No. 60/790,239, filed on Apr. 6, 2006.

(51) Int. Cl.
*A61K 38/00* (2006.01)
*A61K 38/37* (2006.01)
*C07K 14/755* (2006.01)
*C07K 14/435* (2006.01)

(52) U.S. Cl. ......... 530/383; 530/380; 530/381; 424/530

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 4,757,006 A | 7/1988 | Toole et al. | |
| 4,970,300 A | 11/1990 | Fulton et al. | |
| 5,122,614 A | 6/1992 | Zalipsky | |
| 5,153,265 A | 10/1992 | Shadle et al. | |
| 5,198,349 A | 3/1993 | Kaufman | |
| 5,198,493 A | 3/1993 | Holmberg et al. | |
| 5,250,421 A | 10/1993 | Kaufman et al. | |
| 5,298,643 A | 3/1994 | Greenwald | |
| 5,492,821 A | 2/1996 | Callstrom et al. | |
| 5,621,039 A | 4/1997 | Hallahan et al. | |
| 5,733,873 A | 3/1998 | Osterberg et al. | |
| 5,919,766 A | 7/1999 | Osterberg et al. | |
| 5,969,040 A | 10/1999 | Hallahan et al. | |
| 6,037,452 A | 3/2000 | Minamino et al. | |
| 6,048,720 A | 4/2000 | Dahlborg et al. | |
| 6,183,738 B1 | 2/2001 | Clark | |
| 6,586,398 B1 | 7/2003 | Kinstler et al. | |
| 6,692,931 B1 | 2/2004 | Reutter et al. | |
| 6,743,908 B2 | 6/2004 | Filpula et al. | |
| 6,806,063 B2 | 10/2004 | Pedersen et al. | |
| 6,872,393 B2 | 3/2005 | Whitlow et al. | |
| 6,913,915 B2 | 7/2005 | Ensor et al. | |
| 7,118,737 B2 | 10/2006 | Kochendoerfer et al. | |
| 7,199,223 B2 | 4/2007 | Bossard et al. | |
| 7,230,081 B1 | 6/2007 | Jensen et al. | |
| 7,338,788 B2 | 3/2008 | Pedersen et al. | |
| 2003/0143596 A1 | 7/2003 | Bentley et al. | |
| 2005/0106658 A1 | 5/2005 | Defress | |
| 2006/0276634 A1 | 12/2006 | Nakamura et al. | |
| 2007/0244301 A1 | 10/2007 | Siekmann et al. | |
| 2009/0076237 A1 | 3/2009 | Turecek et al. | |

FOREIGN PATENT DOCUMENTS

| | | |
|---|---|---|
| EP | 0306968 | 3/1989 |
| EP | 0605963 | 7/1994 |
| EP | 1258497 | 11/2002 |
| EP | 1260582 | 11/2002 |
| WO | WO-91/09122 | 6/1991 |
| WO | WO-92/16555 | 10/1992 |
| WO | WO-94/05332 | 3/1994 |
| WO | WO-94/15625 | 7/1994 |
| WO | WO-94/15626 | 7/1994 |
| WO | WO-96/40731 | 12/1996 |
| WO | WO-00/23114 | 4/2000 |
| WO | WO-00/48635 | 8/2000 |
| WO | WO-2004/075923 | 9/2004 |
| WO | WO-2004/089280 | 10/2004 |
| WO | WO-2006/071801 | 7/2006 |
| WO | WO-2008/025856 | 3/2008 |
| WO | WO-2008/074032 | 6/2008 |

OTHER PUBLICATIONS

Abuchowski et al., Cancer therapy with chemically modified enzymes. I. Antitumor properties of polyethylene glycol-asparaginase conjugates. *Cancer Biochem. Biophys.* 7: 175-86 (1984).

Baxter announces collaborations to develop longer acting forms of blood clotting factors. *Baxter News* (online), Sep. 29, 2005.

Bi et al., Target disruption of the mouse factor VIII gene produces a model of Haemophilia A. *Nat. Genet.* 10: 119-21 (1995).

Caliceti et al., Pharmacokinetics of pegylated interferons: What is misleading? *Digest. Liver Dis.* 36(Suppl. 3): S334-9 (2004).

Harris et al., Effect of pegylation on pharmaceuticals. *Nat. Rev. Drug Discovery.* 2: 214-21 (2003).

Kozlowski et al., Development of pegylated interferons for the treatment of chronic Hepatitis C. *BioDrugs.* 15(7): 419-29 (2001).

Nektar Advanced PEGylation Catalog 2005-2006, p. 30 (2005).

Nektar Advanced PEGylation Price List 2005-2006, p. 11 (2005).

NOF Corporation DDS Catalogue, p. 58 (2005).

Roberts et a., Chemistry for peptide and protein pegylation *Adv. Drug Del. Rev.* 54: 459-76 (2002).

(Continued)

*Primary Examiner* — Lisa J Hobbs

(74) *Attorney, Agent, or Firm* — Marshall, Gerstein & Borun LLP

(57) ABSTRACT

The invention is a proteinaceous construct comprising a Factor VIII molecule which is conjugated to a water-soluble polymer via carbohydrate moieties of Factor VIII, and methods of preparing same.

22 Claims, 15 Drawing Sheets

OTHER PUBLICATIONS

Rosen et al., Assay of factor VIII: C with a chromogenic substrate. *Scand J. Haematol.* 33(Suppl. 40): 139-45 (1984).

Rostin et al., B-domain deleted recombinant coagulation factor VIII modified with monomethoxy polyethylene glycol. *Bioconjugate Chem.* 11: 387-96 (2000).

Saenko et al., Strategies towards a longer acting factor VIII. *Haemophilia.* 12: 42-51 (2006).

Sakuragawa et al., Studies on the stability of factor VIII modified by polyethylene glycol. *Acta Med. Biol.* 36: 1-5 (1988).

Seffernick et al., Melamine deaminase and atrazine chlorohydrolase: 98% identical but functionally different. *J. Bacteriology.* 2405-10 (2001).

Severs et al., Characterization of PEGylated factor VIII molecules. *Blood.* 108: 11-12 (2006). Abstract.

Study shows molecular size and structure of PEG interferon molecules, as used in pegintron(R), affect antiviral activity in vitro. *Hispanic PR Wire*, Oct. 28, 2003.

Tsubery et al., Prolonging the action of protein and peptide drugs by a novel approach of reversible polyethylene glycol modification. *J. Biol. Chem.* 279(37): 38118-24 (2004).

Tsutsumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA.* 97: 8548-53 (2000).

Urrutigoity et al., Biocatalysis in organic solvents with a polymer-bound horseradish peroxidase. *Biocatalysis.* 2: 145-9 (1989).

Veronese et al., Bioconjugation in pharmaceutical chemistry. *IL Farmaco.* 54: 497-516 (1999).

Wells et al., Additivity of mutational effects in proteins. *Biochemistry.* 29(37): 8509-17 (1990).

Wilchek et al., Labeling glycoconjugates with hydrazide reagents. *Methods Enzymol.* 138: 429-42 (1987).

Zalipsky et al., Hydrazide derivatives of poly(ethylene glycol) and their bioconjugates. Poly(ethylene glycol) Chemistry and Biological Applications. Chapter 21, pp. 318-341 (1997).

International Search Report, PCT/US2007/007560, European Patent Office, dated Sep. 18, 2007.

Written Opinion of the International Search Authority, PCT/US2007/007560, European Patent Office, dated Sep. 18, 2007.

International Search Report, PCT/US2009/052103, European Patent Office, dated Feb. 12, 2010.

Written Opinion of the International Searching Authority, PCT/US2009/052103, European Patent Office, dated Feb. 12, 2010.

FACTOR VIII POLYMER CONJUGATES

This application is a divisional application of U.S. application Ser. No. 12/184,567 filed on Aug. 1, 2008, which is a continuation-in-part of U.S. application Ser. No. 11/729,625, filed on Mar. 29, 2007, which claims priority to U.S. Provisional Application Nos. 60/790,239 and 60/787,968, which were filed on Jun. 6, 2006 and Mar. 31, 2006, respectively.

FIELD OF THE INVENTION

The present invention relates to a proteinaceous construct comprising coagulation factor VIII (FVIII) being bound to at least one water soluble polymer, including a poly(alkylene oxide) such as polyethylene glycol. Further the present invention relates to methods for prolonging the in vivo-half-life of FVIII in the blood of a mammal having a bleeding disorder associated with functional defects or deficiencies of FVIII.

BACKGROUND OF THE INVENTION

Coagulation factor VIII (FVIII) circulates in plasma at a very low concentration and is bound non-covalently to von Willebrand factor (VWF). During hemostasis, FVIII is separated from VWF and acts as a cofactor for activated factor IX (FIXa)-mediated factor X (FX) activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma (e.g., "plasma-derived" or "plasmatic"), FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe haemophilia A with FVIII levels below 1%, are generally on prophylactic therapy with the aim of keeping FVIII above 1% between doses. Taking into account the average half-lives of the various FVIII products in the circulation, this can usually be achieved by giving FVIII two to three times a week.

There are many concentrates on the market for the treatment of hemophilia A. One of these concentrates is the recombinant product Advate®, which is produced in CHO-cells and manufactured by Baxter Healthcare Corporation. No human or animal plasma proteins or albumin are added in the cell culture process, purification, or final formulation of this product.

The aim of many manufacturers of FVIII concentrates and therapeutic polypeptide drugs is to develop a next generation product with enhanced pharmacodynamic and pharmacokinetic properties, while maintaining all other product characteristics.

Therapeutic polypeptide drugs are rapidly degraded by proteolytic enzymes and neutralized by antibodies. This reduces their half-life and circulation time, thereby limiting their therapeutic effectiveness. The addition of a soluble polymer or carbohydrate to a polypeptide has been shown to prevent degradation and increase the polypeptides half-life. For instance, PEGylation of polypeptide drugs protects them and improves their pharmacodynamic and pharmacokinetic profiles (Harris J M et Chess R B, Nat Rev Drug Discov 2003; 2:214-21). The PEGylation process attaches repeating units of polyethylene glycol (PEG) to a polypeptide drug. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation.

Thus, the addition of a soluble polymer, such as through PEGylation is one approach to improve the properties of a FVIII product. The state of the art is documented by different patents and patent applications:

U.S. Pat. No. 6,037,452 describes a poly(alkylene oxide)-FVIII or FIX conjugate, where the protein is covalently bound to a poly(alkylene oxide) through carbonyl-groups of said FVIII.

EP1258497B1 describes a method to prepare conjugates of FVIII and a biocompatible polymer. This patent was supplemented by a publication of Röstin et al. (Bioconj Chem 2000; 11:387-96). The conjugates comprise a B-domain deleted recombinant FVIII modified with monomethoxy polyethylene glycol. The conjugate had reduced FVIII function and the coagulant activity decreased rapidly with the degree of modification.

WO04075923A3 describes polymer-FVIII molecular conjugate comprising a plurality of conjugates wherein each conjugate has one to three water soluble polymers covalently attached to an FVIII molecule. The FVIII molecule is B-domain-deleted.

U.S. Pat. No. 4,970,300 describes a modified FVIII, wherein an infusible conjugate comprising a protein having FVIII activity was covalently linked to a nonantigenic ligand.

U.S. Pat. No. 6,048,720 describes conjugates of a polypeptide and a biocompatible polymer.

WO94/15625 describes FVIII bound to polyethylene glycol having a preferred molecular weight of no greater than 5,000 Daltons.

There remains a need for an FVIII having an attached soluble polymer to extend the half-life of the FVIII in vivo, for example, a PEGylated FVIII, such as full-length FVIII having PEG greater than 10,000 Daltons conjugated thereto, which retains functional activity while providing an extended half-life in vivo, as compared to non-PEGylated FVIII.

SUMMARY OF THE INVENTION

The present invention relates to a proteinaceous construct comprising a Factor VIII molecule which is conjugated to a water-soluble polymer via carbohydrate moieties of Factor VIII, and methods of preparing same.

In one embodiment of the invention, a method of conjugating a water soluble polymer to an oxidized carbohydrate moiety of FVIII is provided comprising contacting the oxidized carbohydrate moiety with an activated water soluble polymer under conditions that allow conjugation. In a related aspect, the water soluble polymer is selected from the group consisting of PEG, PSA and dextran. In still another aspect, the activated water soluble polymer is selected from the group consisting of PEG-hydrazide, PSA-hydrazine and aldehyde-activated dextran. In another aspect of the invention, the carbohydrate moiety is oxidized by incubation in a buffer comprising $NaIO_4$. In still another aspect of the invention, the oxidized carbohydrate moiety of FVIII is located in the B domain of FVIII.

In another embodiment of the invention, a modified FVIII produced by the method according to any of the aforementioned methods is provided. In still another embodiment, a proteinaceous construct is provided comprising (a) a Factor VIII molecule; and (b) at least one water soluble polymer bound to said Factor VIII molecule, wherein the water soluble polymer is attached to the Factor VIII via one or more carbohydrate moieties located in the B domain Factor VIII. In a related aspect of the invention, the water soluble polymer is selected from the group consisting of PEG, PSA and dextran.

FIGURES

FIG. 1 shows the broadening and mass increase of rFVIII after conjugation with PEG measured by SDS-PAGE with subsequent immunoblotting.

FIG. 2 shows the pharmacokinetics of PEG-rFVIII conjugate compared to non-conjugated FVIII in hemophilic mice. Open squares: PEGrFVIII, dose 200 IU FVIII/kg. Closed diamonds: native rFVIII, dose 200 IU FVIII/kg.

DETAILED DESCRIPTION OF THE INVENTION

Figure 1:
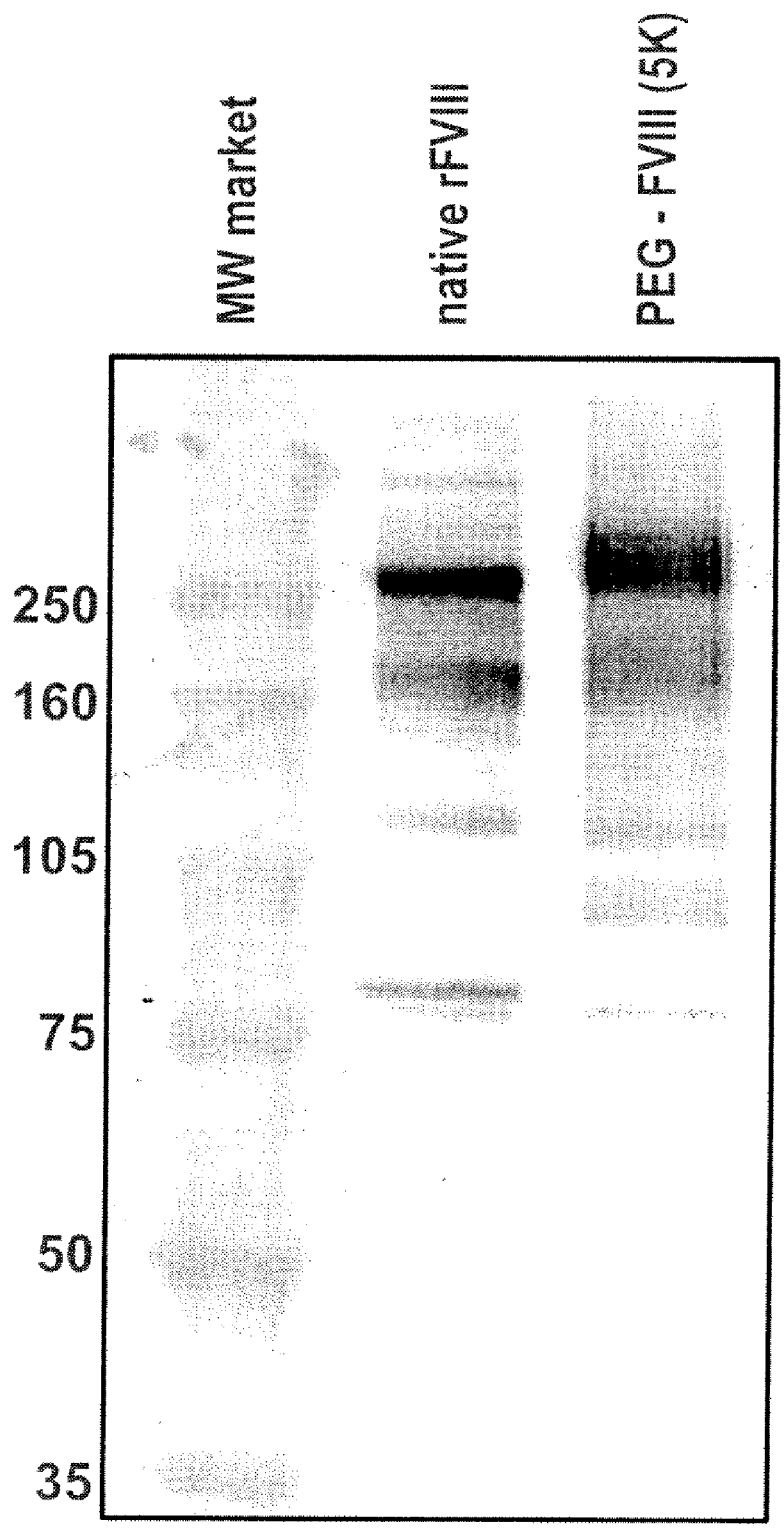

The invention is a proteinaceous construct comprising an FVIII molecule having at least a portion of the B domain intact, bound to a water-soluble polymer which include, a polyalkylene oxide, polyvinyl pyrrolidone, polyvinyl alcohol, polyoxazoline, a poly acryloylmorpholine or a carbohydrate, such as polysialic acid (PSA) or dextran. In one embodiment of the invention, the water soluble polymer is a polyethylene glycol molecule having a molecular weight of greater than 10,000 Daltons. In another embodiment, the water soluble polymer has a molecular weight of greater than 10,000 Da to about 125,000 Da, about 15,000 Da to 20,000 Da, or about 18,000 Da to about 25,000 Da. In one embodiment, the construct retains the full functional activity of standard therapeutic FVIII products, and provides an extended half-life in vivo, as compared to standard therapeutic FVIII products. In another embodiment, the construct retains at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native Factor VIII. In a related aspect, the biological activities of the construct and native Factor VIII are determined by the ratios of chromogenic activity to FVIII antigen value (FVIII:Chr:FVIII:Ag). In still another embodiment of the invention, the half-life of the construct is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native Factor VIII.

The starting material of the present invention is FVIII, which can be derived from human plasma, or produced by recombinant engineering techniques, as described in U.S. Pat. No. 4,757,006; U.S. Pat. No. 5,733,873; U.S. Pat. No. 5,198,349; U.S. Pat. No. 5,250,421; U.S. Pat. No. 5,919,766; EP 306 968.

Herein, the term "Factor VIII" or "FVIII" refers to any FVIII molecule which has at least a portion of the B domain intact, and which exhibits biological activity that is associated with native FVIII. In one embodiment of the invention, the FVIII molecule is full-length Factor VIII. The FVIII molecule is a protein which is encoded for by DNA sequences capable of hybridizing to DNA encoding Factor VIII:C. Such a protein may contain amino acid deletions at various sites between or within the domains A1-A2-B-A3-C1-C2 (U.S. Pat. No. 4,868,112). The FVIII molecule may also be an analog of native FVIII wherein one or more amino acid residues have been replaced by site-directed mutagenesis.

The FVIII molecules useful for the present invention include the full-length protein, precursors of the protein, biologically active or functional subunits or fragments of the protein, and functional derivatives thereof, as well as variants thereof as described herein below. Reference to FVIII is meant to include all potential forms of such proteins and wherein each of the forms of FVIII has at least a portion or all of the native B domain sequence intact.

According to the present invention, the term "recombinant Factor VIII" (rFVIII) may include any rFVIII, heterologous or naturally occurring, obtained via recombinant DNA technology, or a biologically active derivative thereof. In certain embodiments, the term encompasses proteins as described above and nucleic acids, encoding a rFVIII of the invention. Such nucleic acids include, for example and without limitation, genes, pre-mRNAs, mRNAs, polymorphic variants, alleles, synthetic and naturally-occurring mutants. Proteins embraced by the term rFVIII include, for example and without limitation, those proteins and polypeptides described hereinabove, proteins encoded by a nucleic acid described above, interspecies homologs and other polypeptides that: (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids (up to the full length sequence of 406 amino acids for the mature native protein), to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

Polynucleotides encoding a rFVIII of the invention include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein.

As used herein, "endogenous FVIII" includes FVIII which originates from the mammal intended to receive treatment. The term also includes FVIII transcribed from a transgene or any other foreign DNA present in said mammal. As used herein, "exogenous FVIII" includes FVIII which does not originate from said mammal.

Variant (or analog) polypeptides include insertion variants, wherein one or more amino acid residues are added to an FVIII amino acid sequence of the invention. Insertions may be located at either or both termini of the protein, and/or may be positioned within internal regions of the FVIII amino acid sequence. Insertion variants, with additional residues at either or both termini, include for example, fusion proteins and proteins including amino acid tags or other amino acid labels. In one aspect, the FVIII molecule may optionally contain an N-terminal Met, especially when the molecule is expressed recombinantly in a bacterial cell such as *E. coli*.

In deletion variants, one or more amino acid residues in a FVIII polypeptide as described herein are removed. Deletions can be effected at one or both termini of the FVIII polypeptide, and/or with removal of one or more residues within the FVIII amino acid sequence. Deletion variants, therefore, include all fragments of a FVIII polypeptide sequence.

In substitution variants, one or more amino acid residues of a FVIII polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and set out immediately below.

| CONSERVATIVE SUBSTITUTIONS | |
|---|---|
| SIDE CHAIN CHARACTERISTIC | AMINO ACID |
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

| CONSERVATIVE SUBSTITUTIONS II | |
|---|---|
| ORIGINAL RESIDUE | EXEMPLARY SUBSTITUTION |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |

| CONSERVATIVE SUBSTITUTIONS II | |
|---|---|
| ORIGINAL RESIDUE | EXEMPLARY SUBSTITUTION |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

A "naturally-occurring" polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring). Reference polynucleotide and polypeptide sequences include, e.g., UniProtKB/Swiss-Prot P00451 (FA8_HUMAN); Gitschier J et al., Characterization of the human Factor VIII gene, Nature, 312 (5992): 326-30 (1984); Vehar G H et al., Structure of human Factor VIII, Nature, 312(5992):337-42 (1984); and Thompson A R. Structure and Function of the Factor VIII gene and protein, Semin Thromb Hemost, 2003:29; 11-29 (2002), (references incorporated herein in their entireties).

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

As used herein, "plasma-derived FVIII" or "plasmatic" includes all forms of the protein found in blood obtained from a mammal having the property of activating the coagulation pathway.

In various aspects, production of rFVIII includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing rFVIII, e.g. constitutively or upon induction, and (v) isolating said rFVIII, e.g. from the culture medium or by harvesting the transformed cells, in order to (vi) obtain purified rFVIII.

In other aspects, the rFVIII is produced by expression in a suitable prokaryotic or eukaryotic host system characterized by producing a pharmacologically acceptable rFVIII molecule. Examples of eukaryotic cells are mammalian cells, such as CHO, COS, HEK 293, BHK, SK-Hep, and HepG2.

In still other aspects, a wide variety of vectors are used for the preparation of the rFVIII and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

In certain aspects, FVIII molecules are conjugated to a water soluble polymer by any of a variety of chemical methods (Roberts J M et al., Advan Drug Delivery Rev 2002; 54:459-76). For example, in one embodiment FVIII is PEGylated by the conjugation of PEG to free amino groups of the protein using N-hydroxysuccinimide (NHS) esters. In another embodiment the water soluble polymer, for example PEG, is coupled to free SH groups using maleimide chemistry or the coupling of PEG hydrazides or PEG amines to carbohydrate moieties of the FVIII after prior oxidation.

In other embodiments, FVIII is conjugated to other water soluble polymers, where the water soluble polymers are, for example, polyalkylene oxide, polyvinyl pyrrolidone, polyvinyl alcohol, polyoxazoline, a poly acryloylmorpholine, carbohydrate or a polysaccharide such as polysialic acid (PSA) or dextran. The coupling of the water soluble polymer can be carried out by direct coupling to the protein or via linker molecules. One example of a chemical linker is MBPH (4-[4-N-Maleimidophenyl]butyric acid hydrazide) containing a carbohydrate-selective hydrazide and a sulfhydryl-reactive maleimide group (Chamow et al., J Biol Chem 1992; 267: 15916-22).

The conjugation can be performed by direct coupling (or coupling via linker systems) of the water soluble polymer to Factor VIII under formation of stable bonds. In addition degradable, releasable or hydrolysable linker systems can be used in the present invention (Tsubery et al. J Biol Chem 2004; 279:38118-24/Greenwald et al., J Med Chem 1999; 42:3657-67/Zhao et al., Bioconj Chem 2006; 17:341-51/ WO2006/138572A2/U.S. Pat. No. 7,259,224B2/U.S. Pat. No. 7,060,259B2).

As discussed herein, an embodiment of the invention is the coupling of the activated soluble polymer to the oxidized carbohydrate moiety of FVIII. The term "activated water soluble polymer" is used herein to refer to water soluble polymers used for coupling to FVIII having an active functional group, which allows chemical conjugation of the water soluble polymer to a linker or directly to FVIII (which contains an active aldehyde group). The term "oxidized carbohydrate moiety" as used herein refers to FVIII containing free aldehyde groups, which are generated by an oxidative agent such as $NaIO_4$. In one aspect of the invention, aldehyde-activated dextran (containing an active aldehyde groups) is coupled to the aldehyde groups of FVIII via a dihydrazide linker.

According to the glycosylation pattern of FVIII (Lenting et al; *Blood*, 92:3983-96(1998)), conjugation of FVII via carbohydrate moieties should likely take place in the B domain of FVIII. Targeting the B domain for such conjugation reactions is desired since the B domain does not play a role in the activity of FVIII. Enzymatic glycoconjugation is described in US 2008/00700275.

In one embodiment of the invention, FVIII was modified via lysine residues by use of polyethylene glycol derivatives containing an active N-hydroxysuccinimide ester (NHS) such as succinimidyl succinate, succinimidyl glutarate or succinimidyl propionate. These derivatives react with the lysine residues of FVIII under mild conditions by forming a stable amide bond. In one embodiment of the invention, the chain length of the PEG derivative is 5,000 Da. Other PEG derivatives with chain lengths of 500 to 2,000 Da, 2,000 to 5,000 Da, greater than 5,000 up to 10,000 Da or greater than 10,000 up to 20,000 Da, or greater than 20,000 up to 150,000 Da are used in various embodiments, including linear and branched structures.

Alternative methods for the PEGylation of amino groups are the chemical conjugation with PEG carbonates by forming urethane bonds, or the reaction with aldehydes or ketones by reductive amination forming secondary amide bonds.

In the present invention an FVIII molecule is chemically modified using PEG derivatives that are commercially available. These PEG derivatives can have a linear or branched structures. Examples of PEG-derivatives containing NHS groups are listed below.

The following PEG derivatives are examples of those commercially available from Nektar Therapeutics (Huntsville, Ala.; see www.nektar.com/PEG reagent catalog; Nektar Advanced PEGylation, price list 2005-2006):

mPEG-Succinimidyl Propionate (mPEG-SPA)

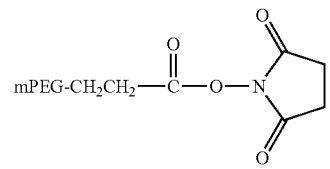

mPEG-Succinimidyl α-Methylbutanoate (mPEG-SMB)

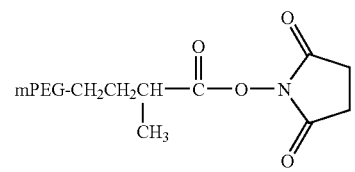

mPEG-CM-HBA-NHS  (CM=Carboxymethyl; HBA=Hydroxy Butyric Acid)

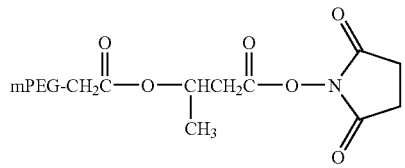

Structure of a Branched PEG-Derivative (Nektar Therapeutics):
Branched PEG N-Hydroxysuccinimide (mPEG2-NHS)

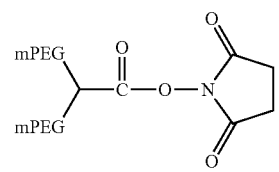

This reagent with branched structure is described in more detail by Kozlowski et al. (BioDrugs 2001; 5:419-29).

Other examples of PEG derivatives are commercially available from NOF Corporation (Tokyo, Japan; see www.nof.co.jp/english: Catalogue 2005)

General Structure of Linear PEG-Derivatives (NOF Corp.):

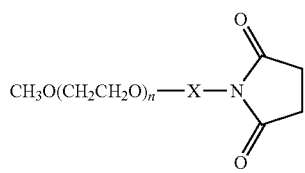

X=carboxymethyl

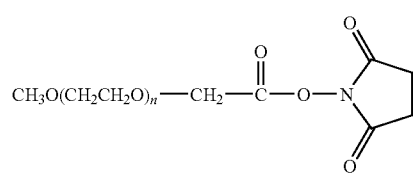

X=carboxypentyl

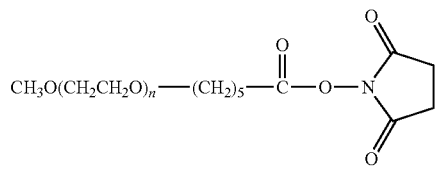

x=succinate

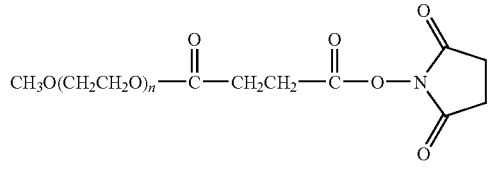

mPEG Succinimidyl succinate x=glutarate

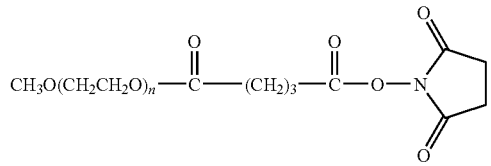

mPEG Succinimidyl glutarate

Structures of Branched PEG-derivatives (NOF Corp.): 2,3-Bis(methylpolyoxyethylene-oxy)-1-(1,5-dioxo-5-succinimidyloxy, pentyloxy)propane

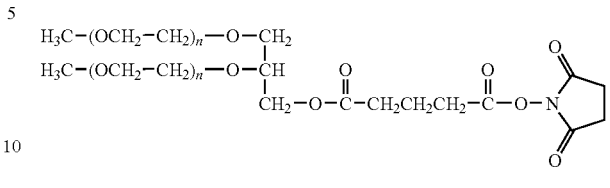

2,3-Bis(methylpolyoxyethylene-oxy)-1-(succinimidyl carboxypentyloxy)propane

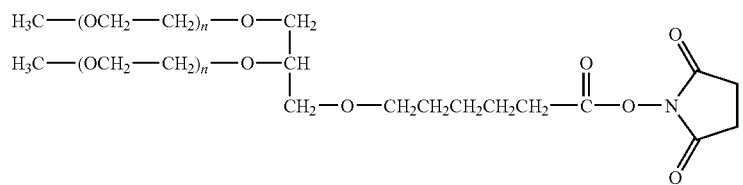

These propane derivatives show a glycerol backbone with a 1,2 substitution pattern. In the present invention branched PEG derivatives based on glycerol structures with 1,3 substitution or other branched structures described in US2003/0143596A1 can also be used.

PEG derivatives with degradable (for example, hydrolysable linkers) as described by Tsubery et al. (J Biol Chem 2004; 279:38118-24) and Shechter et al. (WO04089280A3) can also be used in the present invention.

Surprisingly, the PEGylated FVIII of this invention exhibits full functional activity, combined with an extended FVIII half-life in vivo. In addition the PEGylated rFVIII seems to be more resistant against thrombin inactivation. This was shown by a variety of in vitro and in vivo methods, and is illustrated by the following examples.

As used herein, "sialic acid moieties" includes sialic acid monomers or polymers ("polysaccharides") which are soluble in an aqueous solution or suspension and have little or no negative impact, such as side effects, to mammals upon administration of the PSA-FVIII-conjugate in a pharmaceutically effective amount. There is no particular limitation to the sialic acid unit used according to the present invention. The polymers are characterized, in one aspect, as having from 1 to 4 units. In certain aspects, different sialic acid units are combined in a chain.

In various aspects of the invention, sialic acid moieties are bound to FVIII for example by the method described in U.S. Pat. No. 4,356,170, which is herein incorporated by reference. In various embodiments of the invention, the polysaccharide compound is a naturally occurring polysaccharide, a derivative of a naturally occurring polysaccharide, or a naturally occurring polysaccharide derivative. Generally, all of the saccharide residues in the compound are sialic acid residues.

Other techniques for coupling PSA to polypeptides are also known. For example, US Publication No. 2007/0282096 describes conjugating an amine or hydrazide derivative of, e.g., PSA, to proteins. In addition, US Publication No. 2007/0191597 describes PSA derivatives containing an aldehyde group for reaction with substrates (e.g., proteins) at the reducing terminal end.

In one embodiment of the invention, the polysialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally occurring saccharide compounds, or introduced into derivative polysaccharide compounds.

Polysaccharide compounds of particular use for the invention are, in one aspect. those produced by bacteria. Some of these naturally occurring polysaccharides are known as glycolipids. In one embodiment, the polysaccharide compounds are substantially free of terminal galactose units.

In one embodiment of the present invention, the in vivo half-life of the proteinaceous construct is prolonged. In a related embodiment, the in vivo half-life of the proteinaceous construct is prolonged by at least a factor of two, while in another embodiment the in vivo half-life is prolonged by at least a factor of three, as compared to FVIII which is not bound to a water soluble polymer.

In one embodiment the proteinaceous construct of the present invention may be administered by injection, such as intravenous, intramuscular, or intraperitoneal injection.

To administer compositions comprising a proteinaceous construct of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a mammal having a bleeding disorder as outlined above.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

The present invention also relates to a pharmaceutical composition comprising an effective amount of a proteinaceous construct as defined above. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. Solutions of the pharmaceutical composition may be subjected to any suitable lyophylization process.

As an additional aspect, the invention includes kits which comprise a composition of the invention packaged in a manner which facilitates its use for administration to subjects. In one embodiment, such a kit includes a compound or composition described herein (e.g., a composition comprising a proteinaceous construct), packaged in a container such as a sealed bottle or vessel, with a label affixed to the container or included in the package that describes use of the compound or composition in practicing the method. In one embodiment, the kit contains a first container having a composition comprising a proteinaceous construct and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

EXAMPLES

Example 1

PEGylation of Lysine Residues in rFVIII with mPEG Succinimidyl Succinate

A solution of a rFVIII bulk derived from the Advate manufacturing process (3,400 U/ml) was gel filtrated by use of Econo-Pac 10DG columns (Bio-Rad) using 20 mM Hepes buffer, 150 mM NaCl, pH 7.4, containing 0.5% sucrose and 0.1% Polysorbate 80. Then mPEG Succinimidyl succinate (Abuchowski et al. Cancer Biochim Biophys 1984; 7:175-86) with a chain length of 5,000 Da (PEG-SS 5000) was added to this solution under gentle stirring (5 mg PEG-SS/mg protein) and the pH value was adjusted to 7.4 by drop wise addition of 0.5 M NaOH. Then the PEGylation was carried out under gentle stirring for 1 hour at room temperature.

Subsequently the reaction mixture was applied onto an equilibrated ion-exchange chromatography resin (Fractogel EMD TMAE 650M/Pharmacia XK-10 column, bed height: 15.0 cm) in 20 mM Hepes buffer, 150 mM NaCl, pH 7.4, containing 0.5% sucrose and 0.1% Polysorbate 80. Then the column was washed with 20 CV equilibration buffer to remove excess reagent and the PEGylated rFVIII was eluted with elution buffer (20 mM Hepes, 1.0 M NaCl, 0.5% sucrose, 0.1% Polysorbate 80, pH 7.4). The eluate was concentrated by ultrafiltration/diafiltration with a membrane consisting of regenerated cellulose and with a molecular weight cut-off of 30 kD using a buffer system consisting of 20 mM Hepes, 150 mM NaCl, 0.5% sucrose, pH 7.4.

Example 2

Biochemical Characterization of PEGylated rFVIII In Vitro

RFVIII derived from the Advate manufacturing process was PEGylated according to Example 1 and the PEGylated FVIII product was biochemically characterized. The functional activity of the PEG-rFVIII was determined by use of the FVIII chromogenic assay (Rosen S, Scand J Haematol 1984; 33 (Suppl 40):139-45). The method is based on Ph. Eur. 5th edition (5.05) 2.7.4 Assay of Blood Coagulation Factor VIII.

A sample, containing factor VIII (FVIII:C) is mixed with thrombin, activated factor IX (FIXa), phospholipids and factor X (FX) in a buffer containing calcium. FVIII is activated by thrombin and subsequently forms a complex with phospholipids, FIXa and calcium ions. This complex activates factor X to factor Xa, which in turn cleaves the chromogenic substrate FXa-1 (AcOH*CH3OCO-D-CHA-Gly-Arg-pNA). The time course of para-nitroaniline (pNA) released is measured with a micro plate reader at 405 nm. The slope of the reaction is proportional to the factor VIII concentration in the sample. The FVIII antigen value was measured by use of an ELISA system commercially available (Cedarlane, Hornby, Ontario, Canada) with minor modifications. From these values the ratios FVIII chromogen/FVIII antigen were calculated. The protein content in the preparations was determined by measuring the optical density at 280 nm. From these data the protein content was calculated (Hoyer L W in: Human Protein Data. Installments 1-6; Heberli Ed.; Wiley V C H, Weinheim, Germany, 1998) and expressed in mg/ml.

TABLE 1

|  | Native rFVIII | PEG-rFVIII PEG-SS 5K (5 mg per mg protein) |
|---|---|---|
| FVIII: Chr activity [U/ml] | 3,430 | 64 |
| FVIII: Ag [U/ml] | 4,067 | 81 |
| Ratio FVIII: Chr/FVIII: Ag | 0.84 | 0.79 |
| Recovery of biological activity (%) | 100 | 94 |

The data in Table 1 shows that in the PEGylated rFVIII preparation, the biological activity (expressed by the ratio FVIII chromogenic activity to FVIII antigen) is recovered to more than 90% in comparison to the biological activity of the native rFVIII (100%).

Example 3

Characterization of PEGylated rFVIII by SDS-PAGE and Immunoblotting Techniques

Native rFVIII was characterized by SDS PAGE under reducing conditions by using a 4-12% polyacrylamide gradient gel obtained from Invitrogen (Carlsbad, Calif., USA) according to the instructions of the manufacturer. As molecular weight markers (MW) Precision Plus markers (10 kD-250 kD) obtained from Bio-Rad (Hercules, Calif., USA) were used. Then the proteins were transferred on a PVDF membrane obtained from Bio-Rad (Hercules, Calif., USA) by electroblotting and subsequently incubated with a polyclonal sheep anti human FVIII:C antibody obtained from Cedarlane (Hornby, Ontario, Canada). The last steps of the immunostaining procedure were the incubation with an alkaline phosphatase (ALP) conjugated anti-sheep antibody obtained from Accurate (Westbury, N.Y., USA) followed by the final visualization by use of an ALP substrate kit (Bio-Rad, Hercules, Calif., USA). The results are summarized in FIG. 1. The blot demonstrates the domain structure of native and PEGylated rFVIII. It is shown that the PEGylated rFVIII has broader bands and high molecular masses than the native recombinant protein.

Example 4

Pharmacokinetics of PEGylated rFVIII in a FVIII Deficient Knock Out Mouse Model

Figure 2:
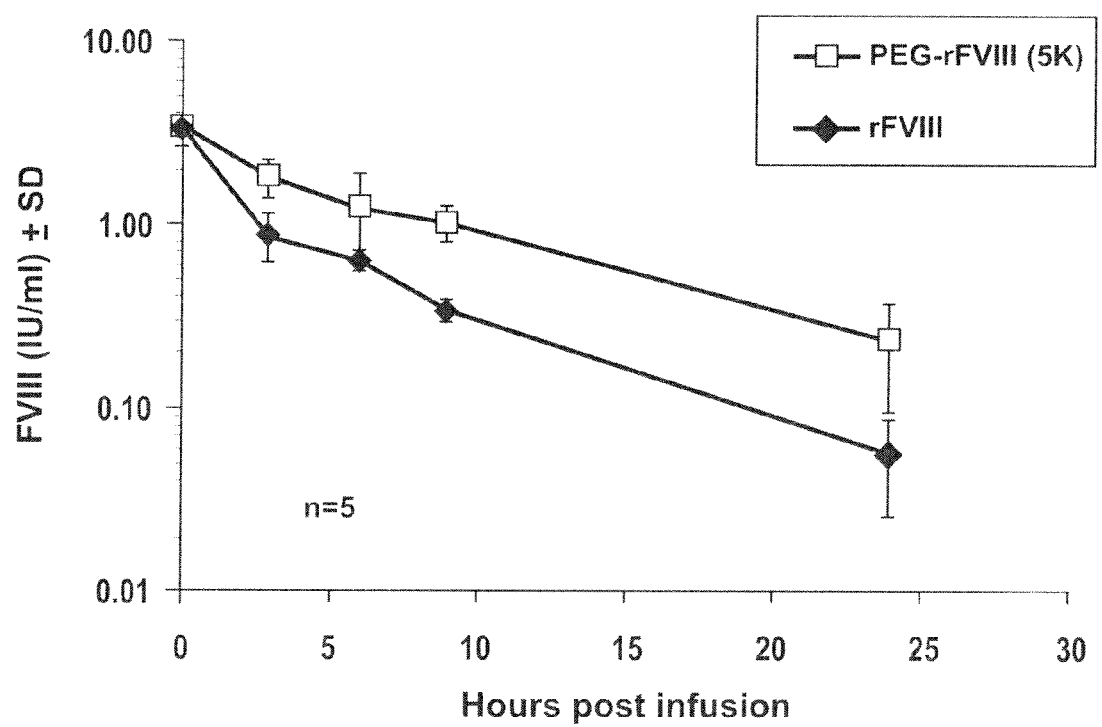
Figure 3A:
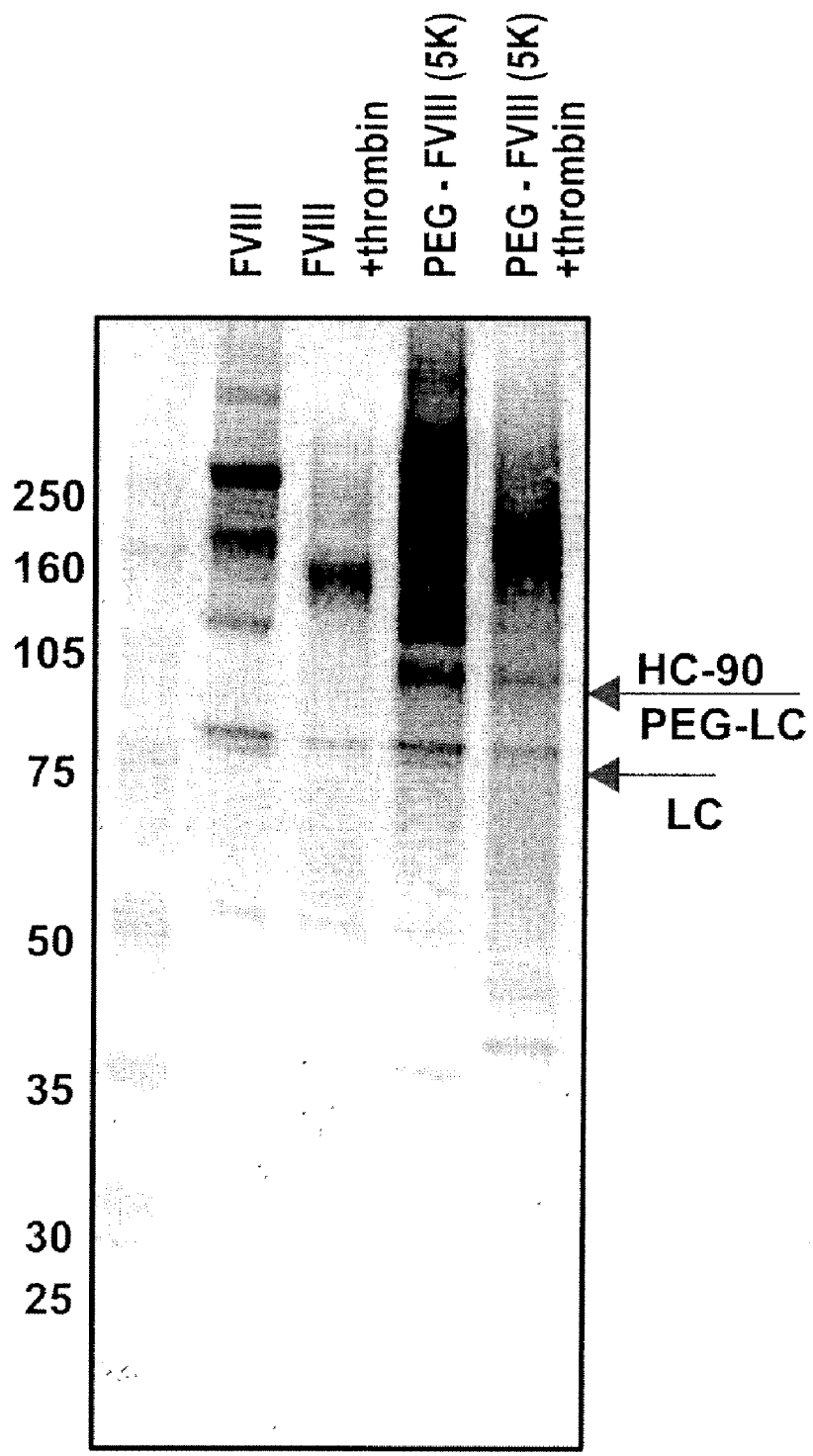
FIGS. 3A-3E show the detailed analysis of PEGylation sites by SDS-PAGE using various anti FVIII antibodies.
Figure 3B:
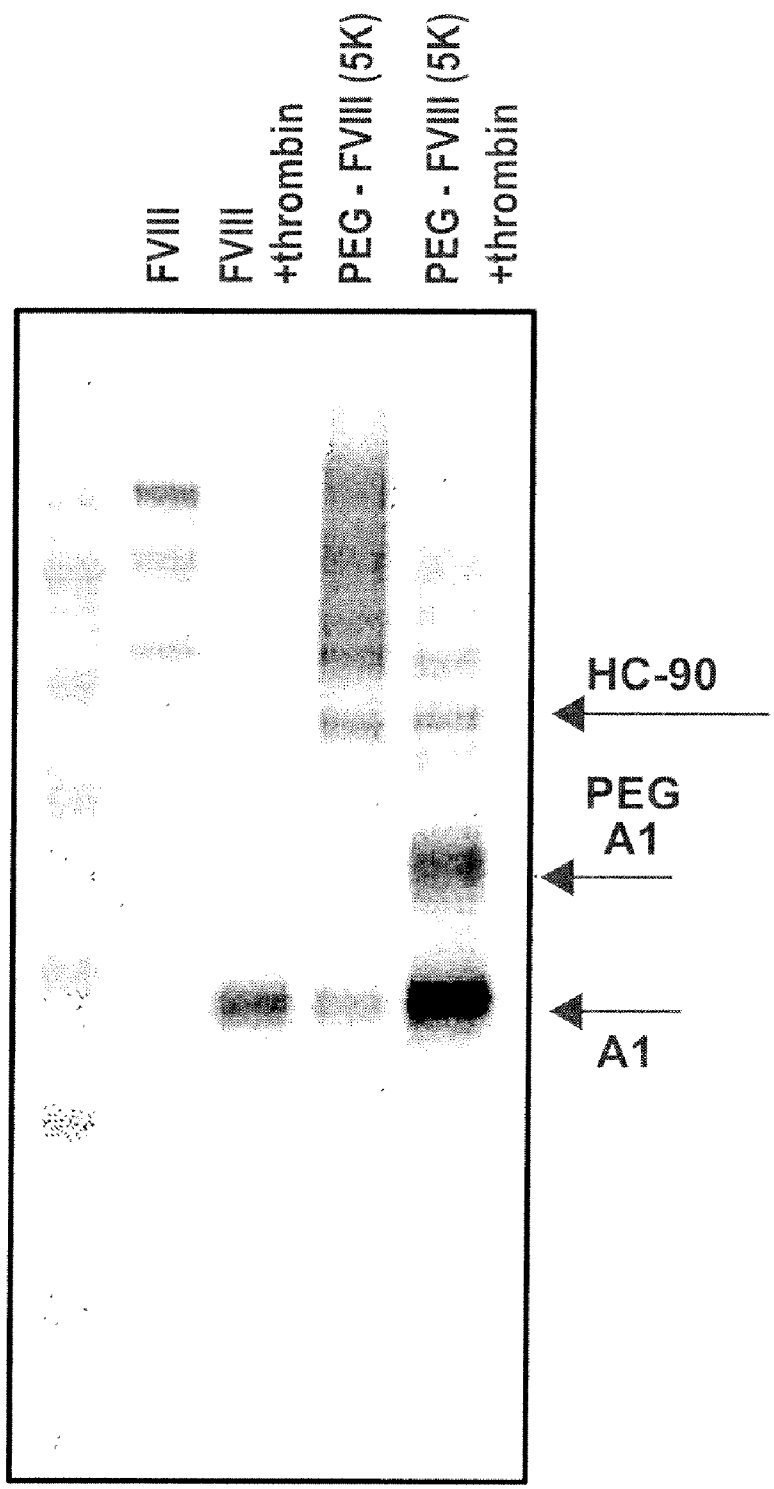
Figure 3C:
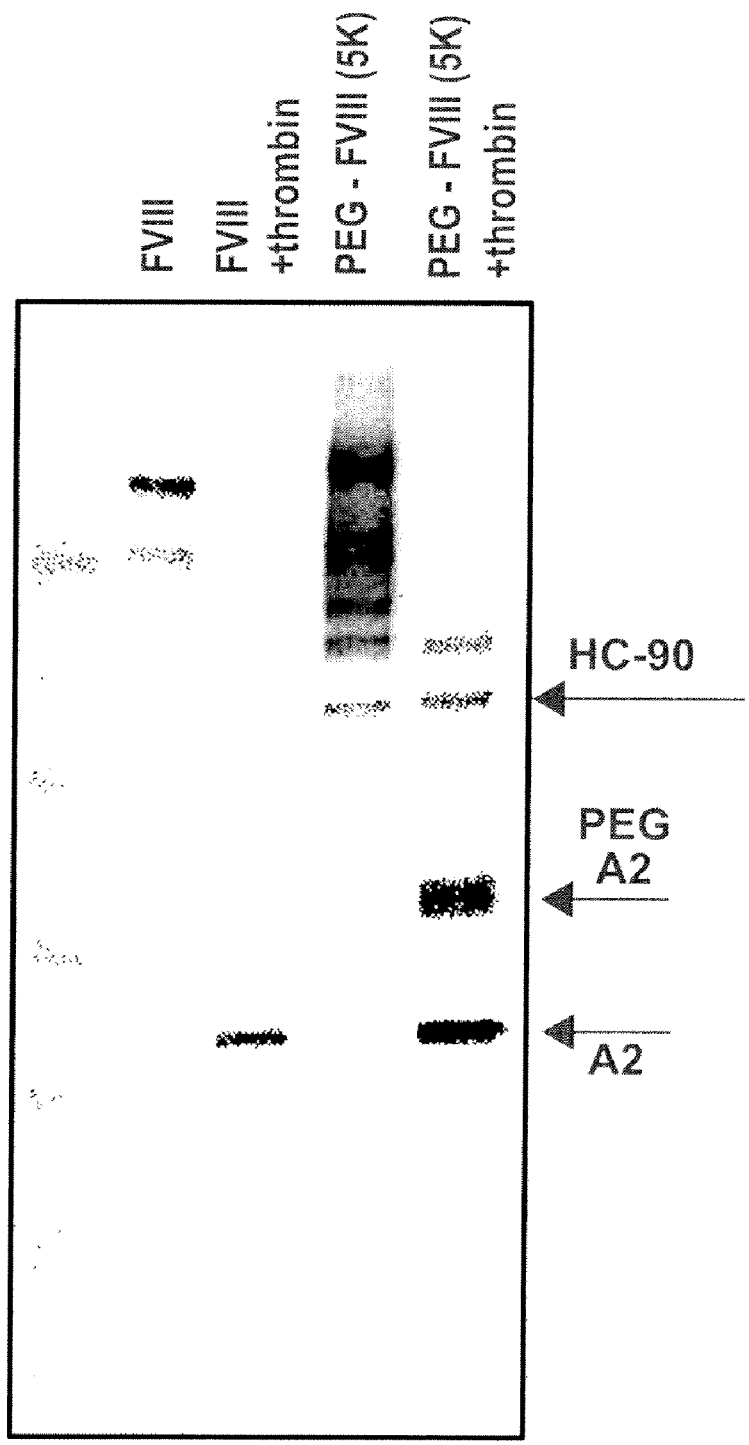
Figure 3D:
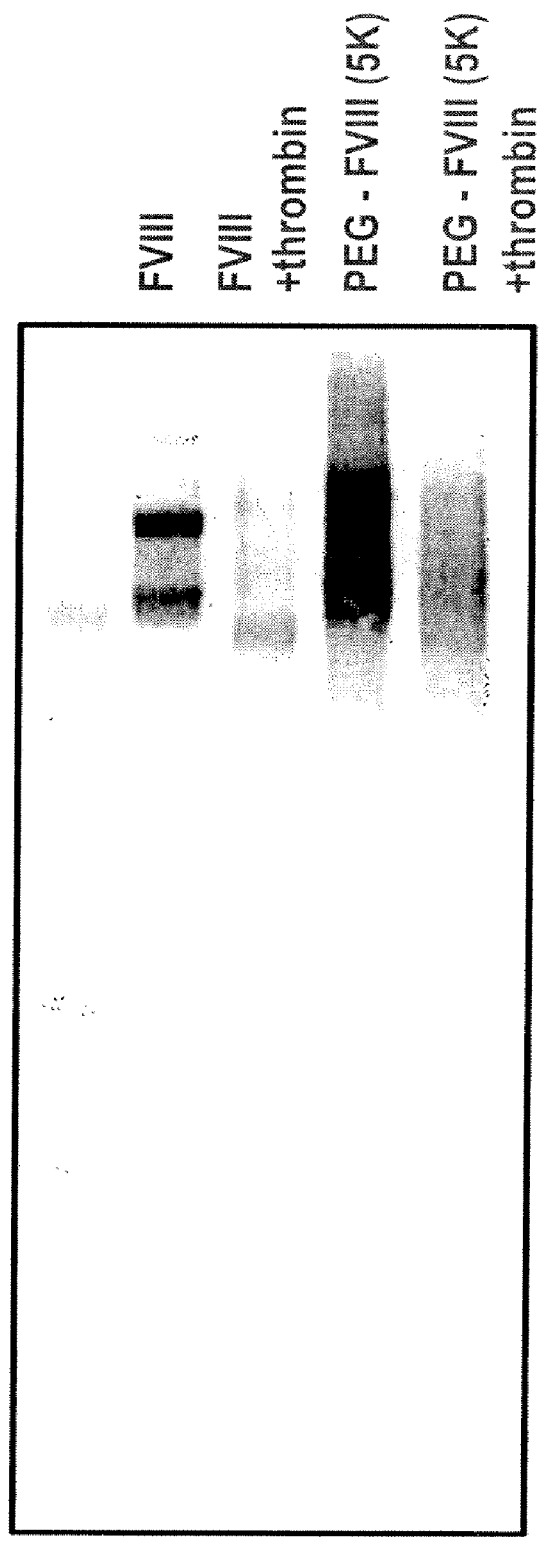
Figure 3E:
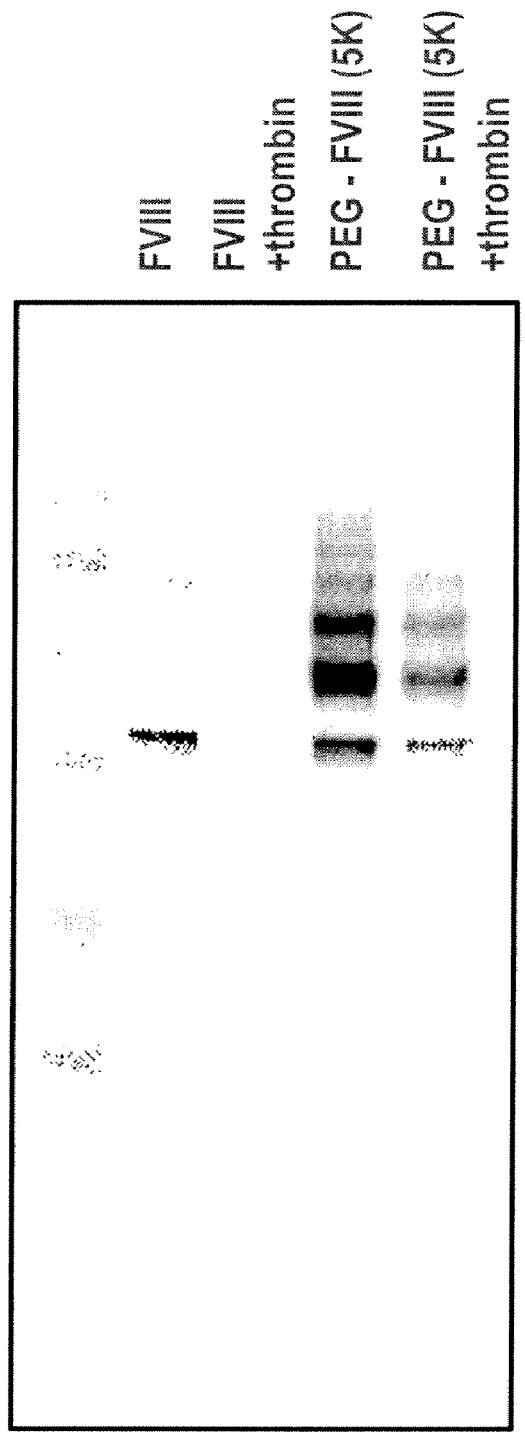

FVIII deficient mice described in detail by Bi et al. (Nat Genet 1995; 10:119-21) were used as a model of severe human hemophilia A. Groups of 5 mice received a bolus injection (10 ml/kg) via the tail vein with either PEG-rFVIII (PEG-SS, 5K) prepared according to Example 1 or native rFVIII in a dose of 200 IU FVIII/kg bodyweight. Citrate plasma by heart puncture after anesthesia was prepared from the respective groups, 5 minutes, 3, 6, 9 and 24 hours after injection. FVIII activity levels were measured in plasma samples. The results of this experiment are summarized in FIG. 2. Mean half life increased from 1.9 hours (for native rFVIII) to 4.9 hours (for PEGylated rFVIII), area under curve (AUC) increased from 13.0 to 25.2 hours*IU/ml. Half-life calculation was performed with MicroMath Scientist, model 1 from pharmacokinetic library (MicroMath, Saint Louis, Mo., USA).

Example 5

Detailed Analysis of PEGylation of rFVIII by SDS-PAGE and Immunoblotting Techniques Native and PEGylated rFVIII was digested with 1 nM thrombin for 60 minutes at 60° C., which resulted in specific cleavage of the FVIII molecule with well defined degradation products. These heavy- and light chain fragments were separated by SDS-PAGE followed by electroblotting, as described in Example 3. To visualize the cleaved fragments, a polyclonal antibody and monoclonal antibodies against the heavy chain A1 and A2 domains, the B domain and the light chain N-terminal A3 domain were applied.

As seen in FIG. 3 all domains were PEGylated, albeit to a different extent. The B domain was strongly PEGylated. Both the A1 and A2 domains of the heavy chain were partially PEGylated. Various PEGylation-degrees (mono-, di-, tri- . . . ) could be observed in the light chain A3-domain. In agreement with Example 6, the PEGylated FVIII seemed to be more resistant to thrombin.

Example 6

Thrombin-Resistancy of PEGylated rFVIII

In vitro thrombin treatment of FVIII results in a rapid increase and subsequent decrease in its procoagulant activity. The rate of activation and inactivation, which depends on the thrombin concentration and on the integrity of FVIII, was monitored by a FIXa cofactor assay, as follows:

FVIII was incubated at 37° C. with 0.5 or 1 nM thrombin. Subsamples were withdrawn at time intervals between 0.5 to 40 minutes and added to a mixture of FIXa, FX, PL-vesicles and $CaCl_2$ also containing a specific thrombin inhibitor to stop the further thrombin-mediated reactions and incubated for 3 minutes. A subsample was added to a chromogenic substrate, which is selectively cleaved by FXa and contained EDTA to stop further Xa activation. After a 15 min incubation, the reaction was terminated by acetic acid. The absorbance (A405) values, which are proportional to the FXa concentrations, were measured in an ELISA reader and converted to FXa concentrations using a purified FXa reference curve. The generated FXa concentrations were plotted against the incubation time with thrombin.

Pseudo-first order inactivation rate of FVIII was determined by fitting the declining part of the curves with a single exponential fit.

TABLE 2

First order inactivation Rate k' (1/min)

| Thrombin | Native FVIII | PEG-FVIII | Relative k' PEG/native |
|---|---|---|---|
| 0.5 nM | 0.14 | 0.08 | 0.57 |
| 1 nM | 0.24 | 0.14 | 0.58 |

Figure 4A:
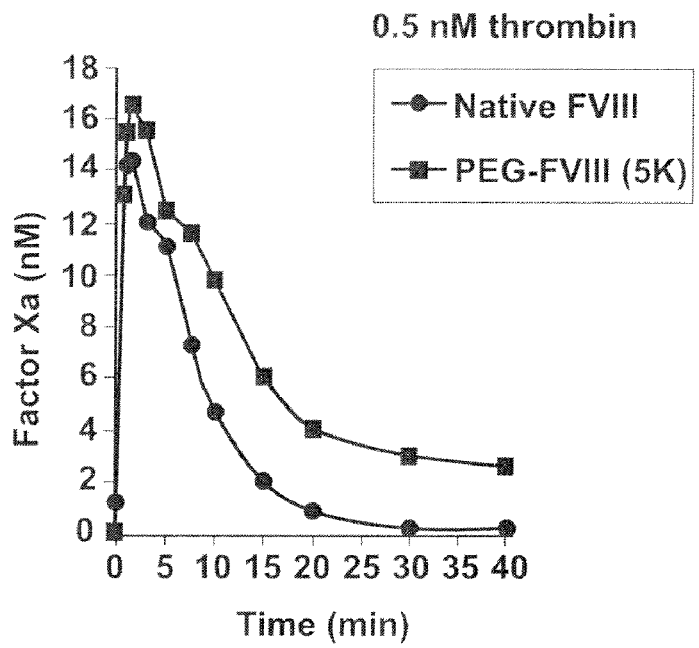
FIGS. 4A-4B show the thrombin-induced activation and inactivation of native and PEGylated rFVIII.
Figure 4B:
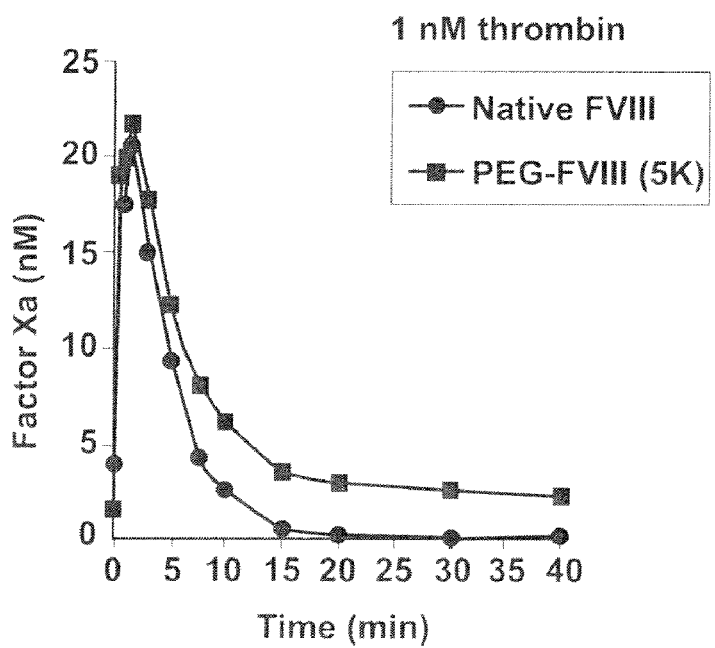

As shown in FIG. 4 and Table 2, PEGylated rFVIII showed a slower inactivation rate at both applied thrombin concentrations.

Example 7

PEGylation of Lysine Residues in rFVIII with Branched 2,3-Bis(methylpolyoxyethylene-oxy)-1-(1,5-dioxo-5-succinimidyloxy, pentyloxy)propane A solution of rFVIII in 20 mM Hepes buffer pH 7.4 containing 150 mM NaCl, 0.5% sucrose and 0.1% Polysorbate 80 was prepared from bulk material derived from the Advate manufacturing process containing 489 IU FVIII/ml. A branched PEG succinimidyl glutarate (PEG-SG) reagent (2,3-Bis(methylpolyoxyethylene-oxy)-1-(1,5-dioxo-5-succinimidyloxy, pentyloxy) propane) obtained from NOF Corporation (Tokyo, Japan) with a molecular weight of 20 kD was added to 153 ml of this solution under gentle stirring (5 mg reagent/mg protein) and the pH value was adjusted to 7.4 by drop wise addition of 0.5 M NaOH after 10 minutes. Then the PEGylation of rFVIII was performed under gentle stirring for 1 hour at room temperature.

Subsequently the reaction mixture was applied onto an equilibrated ion-exchange chromatography resin (Fractogel EMD TMAE 650M/Pharmacia XK-50 column, bed height: 14.5 cm) in 20 mM Hepes buffer, 150 mM NaCl, pH 7.4, containing 0.5% sucrose and 0.1% Polysorbate 80 using a linear flow rate of 1 cm/min. The column was washed with 25 CV equilibration buffer to remove excess reagent (linear flow rate: 2 cm/min) and the PEGylated rFVIII was eluted with elution buffer (20 mM Hepes, 1.0 M NaCl, 0.5% sucrose, 0.1% Polysorbate 80, pH 7.4) at a linear flow rate of 0.5 cm/min. Then the eluate was concentrated by ultrafiltration/diafiltration with a membrane consisting of regenerated cellulose and with a molecular weight cut-off of 30 kD using a buffer system consisting of 20 mM Hepes, 150 mM NaCl, 0.5% sucrose, pH 7.4.

Example 8

In-Vitro Characterization of rFVIII PEGylated with Branched PEG-SG 20 kD

RFVIII derived from the Advate manufacturing process was PEGylated via lysine residues using a branched PEG-SG reagent according to Example 7 and the PEGylated rFVIII product was biochemically characterized as described in Example 2.

TABLE 3

| | Native rFVIII | PEG-rFVIII PEG-SG 20K (5 mg per mg protein) |
|---|---|---|
| FVIII: Chr activity [U/ml] | 9,950 | 1,040 |
| FVIII: Ag [U/ml] | 20,807 | 1,763 |
| Ratio FVIII: Chr/FVIII: Ag | 0.48 | 0.59 |
| Recovery of biological activity (%) | 100 | 120 |

The data in Table 3 show that in the PEGylated rFVIII preparation the biological activity (expressed by the ratio FVIII chromogenic activity to FVIII antigen) completely recovered in comparison to the biological activity of the native rFVIII (100%).

Figure 5:
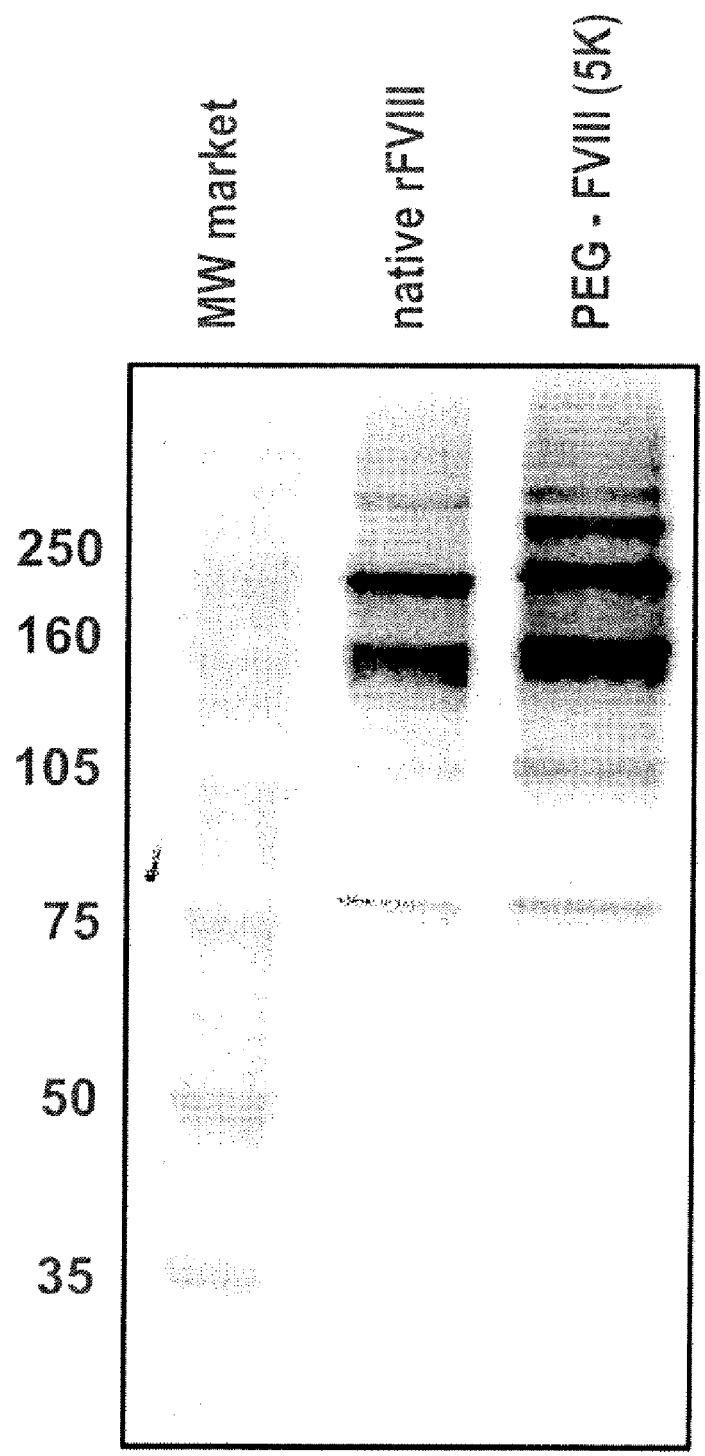
FIG. 5 shows the bands demonstrating the domains of native and PEGylated rFVIII.
Figure 6A:
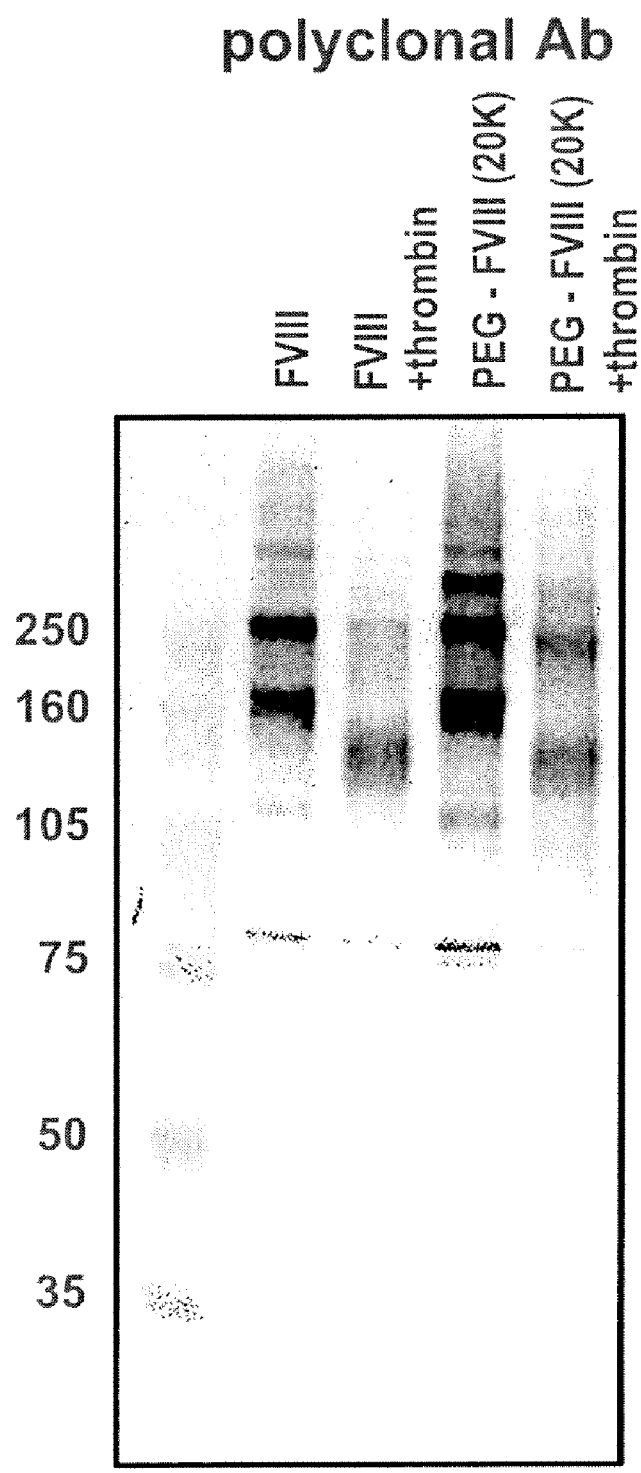
FIGS. 6A-6E show the extent of PEGylation of various domains of native and PEGylated rFVIII. rFVIII.
Figure 6B:
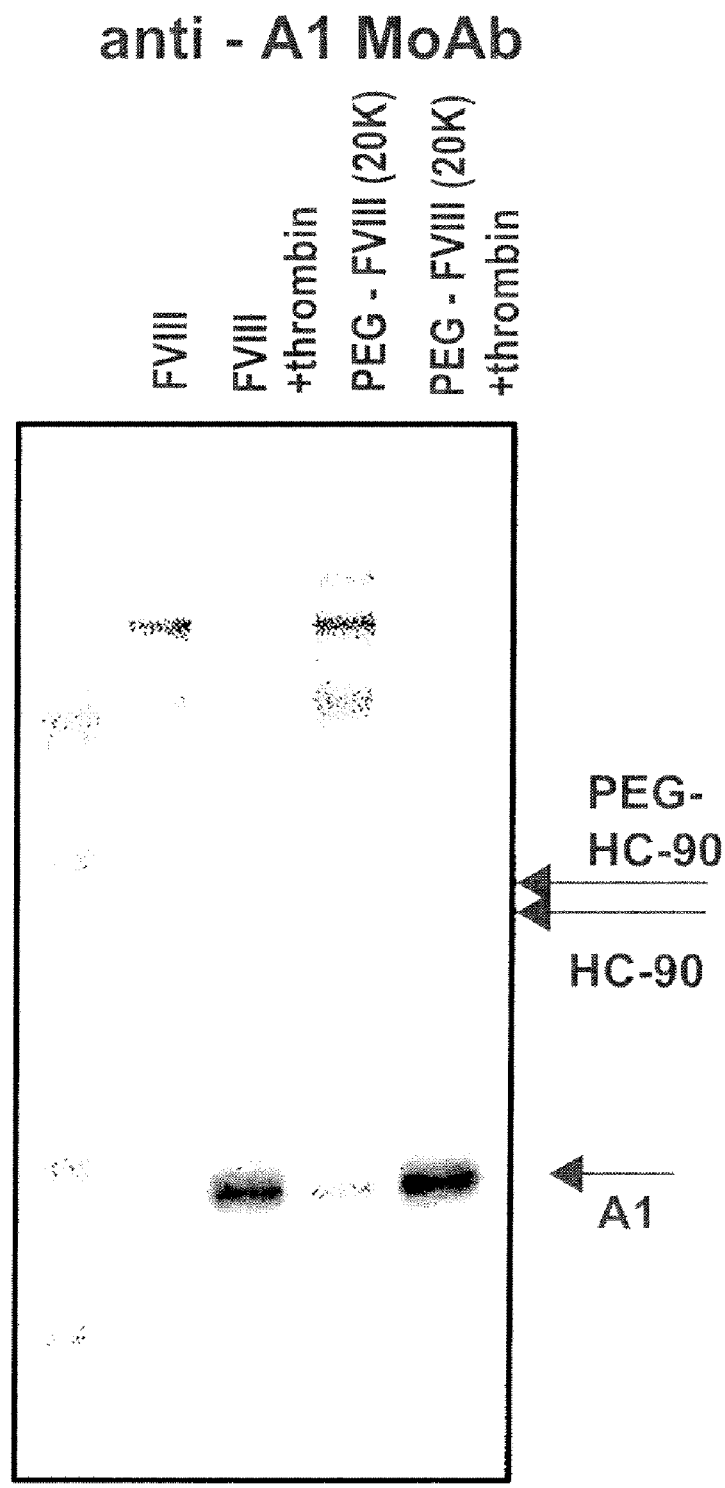
Figure 6C:
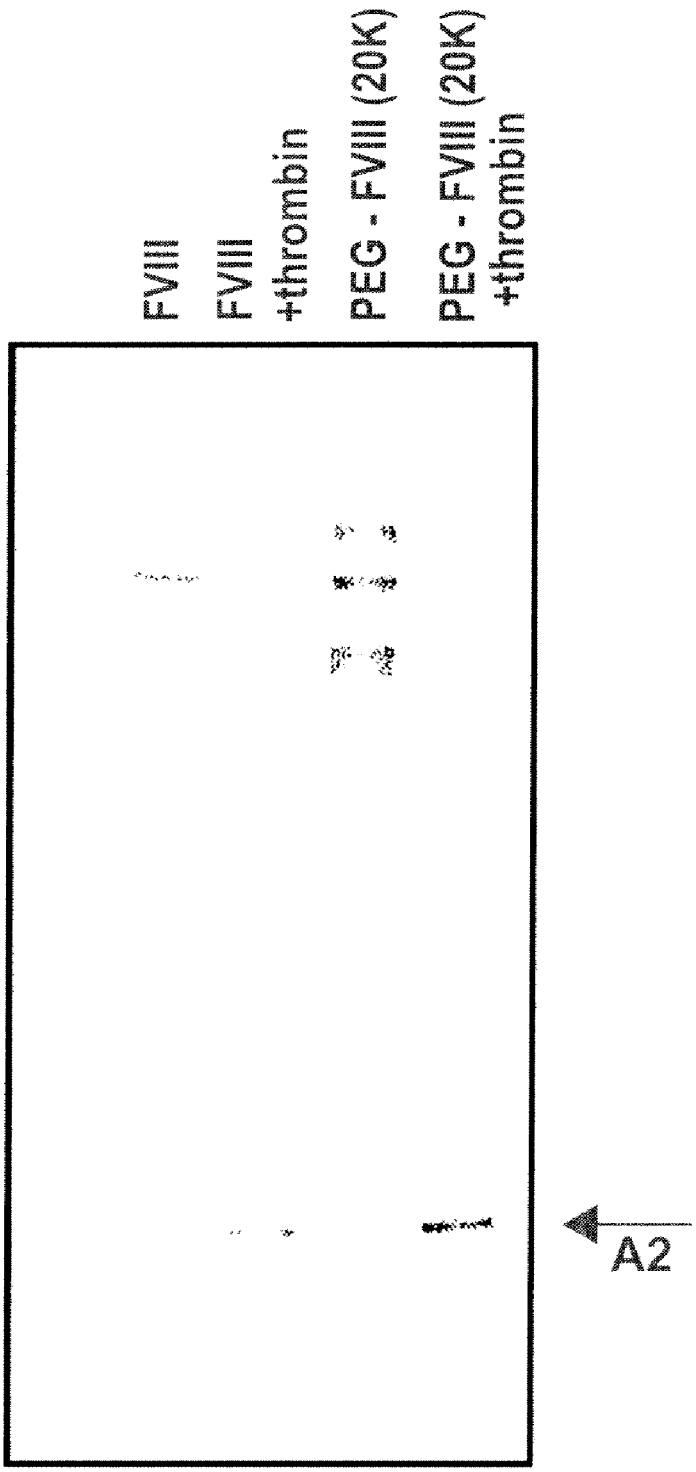
Figure 6D:
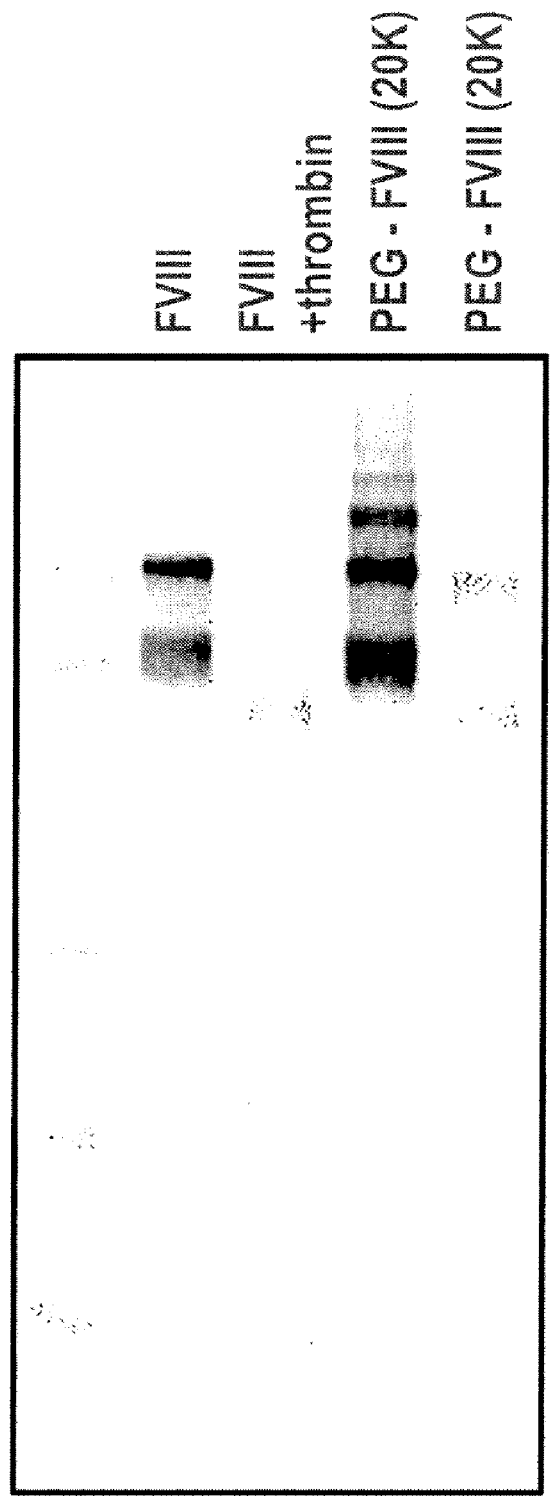
Figure 6E:
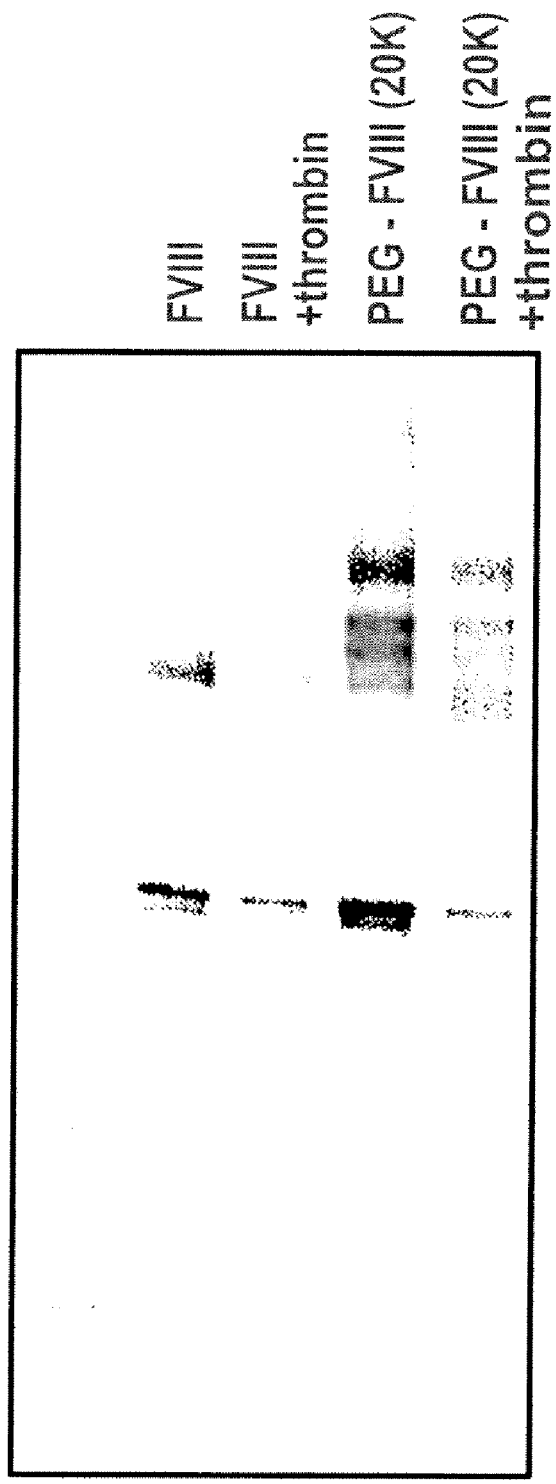

The PEGylated rFVIII was characterized by SDS-PAGE and immunoblotting techniques under reducing conditions using a 4-12% polyacrylamide gradient gel as described in Example 3. The results are summarized in FIG. 5. The blot demonstrates the domain structure of native and PEGylated rFVIII. It is shown that the PEGylated rFVIII has broader bands and high molecular masses than the native recombinant protein.

For more detailed analysis of PEGylation of the rFVIII preparation by SDS-PAGE and immunoblotting techniques, the native and PEGylated rFVIII was digested with 1 nM thrombin for 60 minutes at 60°, which resulted in specific cleavage of the FVIII molecule with well defined degradation products, as described in Example 5. The fragments were separated by SDS-PAGE followed by electroblotting and visualized by different anti-FVIII antibodies. As seen in FIG. 6, all domains were PEGylated, albeit to a different extent. The B domain was strongly PEGylated. Various PEGylation-degrees (mono-, di-, tri-PEGylation) could be observed in the light chain A3-domain. The results indicate that the PEGylated rFVIII seemed to be more resistant to thrombin.

The rate of activation and inactivation by thrombin was monitored by a FIXa cofactor assay as described in Example 6. Pseudo-first order inactivation rate of FVIII was determined by fitting the declining part of the curves with a single exponential fit.

TABLE 4

First order inactivation Rate k' (1/min)

| Thrombin | Native FVIII | PEG-FVIII | Relative k' PEG/native |
|---|---|---|---|
| 0.5 nM | 0.13 | 0.09 | 0.67 |
| 1 nM | 0.21 | 0.15 | 0.71 |

Figure 7A:
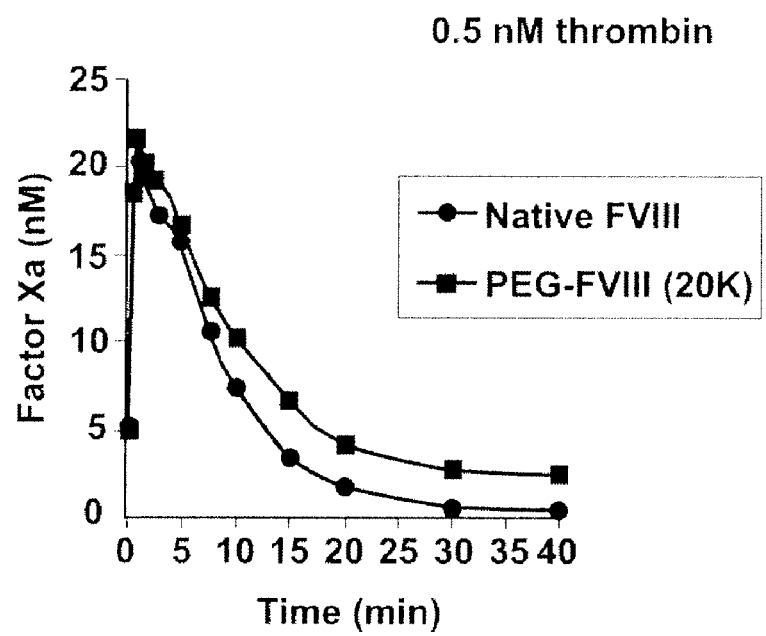
FIGS. 7A-7B show the thrombin inactivation rate of native and PEGylated
Figure 7B:
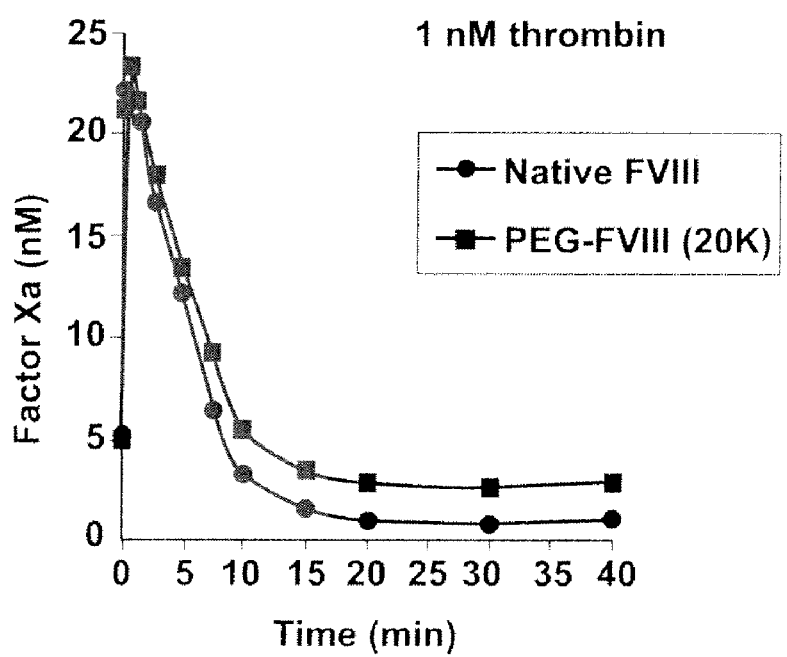

As shown in FIG. 7 and Table 4, the PEGylated rFVIII showed a slower inactivation rate at both applied thrombin concentrations.

Example 9

PEGylation of rFVIII Via Carbohydrate Moiety

For preparation of a PEGrFVIII conjugate via carbohydrate residues, a solution of rFVIII (final concentration: 1.2 mg/ml) is prepared in 25 mM phosphate buffer, pH 6.7. NaIO$_4$ is added (final concentration 0.3 mM) for the oxidation of carbohydrate residues (Roberts et al.; *Advanced Drug Del*

Rev.; 54:459-76 (2002); Meir and Wilchek; *Meth Enzymol;* 138: 429-42(1987)). The reaction was quenched by addition of glycerol in a final concentration of 10%, and the excess reagents were separated by repeated centrifugation using Amicon Micron-10 devices (Amicon, Billerica, Mass.). PEG-hydrazide (MW 3300 Da/Nektar, Huntsville, Ala.) was added to give a final concentration of 1.5 mM reagent. The PEGylation was then performed for 2 h at room temperature. Subsequently, the conjugate obtained and the excess reagent was separated by repeated centrifugation on Amicon Micron-10 devices using 25 mM phosphate buffer, pH 6.7.

Example 10

Polysialylation of rFVIII with PSA-Hydrazine

For preparation of a PSA-rFVIII conjugate via carbohydrate residues, a solution of rFVIII (final concentration: 1 mg/ml) is prepared in 20 mM sodium acetate buffer, pH 6.0. $NaIO_4$ is added (final concentration 0.25 mM) for the oxidation of carbohydrate residues. The oxidation is carried out for 60 min at 4° C. in the dark. Sodium bisulfite (final concentration 25 mM) is added to stop the reaction. The excess sodium periodate is separated by gelfiltration on DG-10 columns (Bio-Rad). Subsequently, PSA-hydrazine with a chain length of 20 kD (prepared according to WO2006/016168) is added (final concentration 10 mM). The polysialylation procedure is carried out for 2 h at room temperature. The polysialylated rFVIII is purified by HIC on Butyl-Sepharose (GE-Healthcare). A 5 M NaCl solution is added to the mixture to give a final concentration of 3M NaCl. This mixture is applied to the column filled with Butyl-Sepharose (GE-Healthcare) and the elution of the rFVIII-PSA conjugate is carried out with 50 mM Hepes-buffer, pH 7.4, containing 6.7 mM $CaCl_2$. After elution of the conjugate, the pH is adjusted to pH 6.9.

Example 11

Purification and Derivatization of Polysialic Acid

Polysialic Acid was purified by anion-exchange chromatography on Q-Sepharose FF as described in WO06016161A1. Five grams of PSA were dissolved in 50 mL 10 mM Triethanolamine buffer, pH 7.4 containing 25 mM NaCl (=starting buffer). This solution was applied onto a Pharmacia XK50 column filled with Q-Sepharose FF (GE Healthcare, Munich, Germany), which was equilibrated with starting buffer. The column was next washed with 8 column volumes (CV) starting buffer and the bound PSA was eluted stepwise with 3CV 200 mM NaCl, 350 mM NaCl and 500 mM NaCl in starting buffer. The fraction eluted with 350 mM NaCl showed a molecular weight of 20 kDa as indicated by SDS gel electrophoresis. This fraction was concentrated by ultrafiltration using a 5 kD membrane made of regenerated cellulose (Millipore, Billerica, Mass.) and subsequently diafiltrated against 50 mM phosphate buffer, pH 7.2. The PSA was oxidized with $NaIO_4$ and a terminal primary amino group was introduced by reductive amination as described in WO05016973A1. For reductive amination, 11 mL of a 2 M $NH_4Cl$ solution were added to 20 mL of a solution containing 58 mg oxidized PSA/ml in 50 mM phosphate buffer, pH 7.2. A solution of 5M $NaCNBH_3$ in 1M NaOH was then added to give a final concentration of 75 mM. The reaction was performed for 5d at room temperature at pH 8.0.

The mixture was then dialyzed against a $(NH_4)_2CO_3$ solution (50 mg/L) containing 10 mM NaCl and subsequently against 50 mM phosphate buffer, pH 8.0, containing 5 mM EDTA. A sulfhydryl group was next introduced by reaction of the terminal primary amino group with 2-iminothiolane (Traut's reagent/Pierce, Rockford, Ill.). The reaction was carried out in 50 mM phosphate buffer, pH 8.0, containing 5 mM EDTA with 20 fold molar excess of reagent for 1 h at room temperature. Finally the PSA solution containing a terminal free SH-group was subjected to ultrafiltration/diafiltration using a membrane with a cut-off of 5 kD and made of regenerated cellulose (Millipore, Billerica, Mass.).

Example 12

Polysialylation of rFVIII by Use of a Heterobifunctional Cross-Linker

For coupling of PSA-SH to rFVIII, the heterobifunctional cross-linker MBPH (4-[4-N-Maleimidophenyl]butyric acid hydrazide·HCl/Pierce, Rockford, Ill.) containing a carbohydrate-selective hydrazide and a sulfhydryl-reactive maleimide group was used (Chamow et al., J Biol Chem; 267:15916-22(1992)). PSA-SH containing an active sulfhydryl group was prepared according to Example 11.

Two ml rFVIII (638 mg, 3.856 mg/ml protein concentration) were transferred to oxidation buffer (50 mM sodium acetate, pH 6) using desalting columns (Bio-Rad Econopac 10 DG) according to the instructions of the manufacturer. The protein was then oxidized with 0.25mM $NaIO_4$ (Merck) (1 h at 4° C. in the dark). The oxidation reaction was quenched with glycerol in a final concentration of 10%. Glycerol and $NaIO_4$ were removed and the protein was transferred into reaction buffer (50 mM sodium phosphate pH 6.5) using desalting columns (Bio-Rad Econopac 10 DG) according to the manufacturer's instructions. A mixture containing 1 mg MBPH/mg protein and PSA-SH (200 fold molar excess to protein) were next incubated for 2 h at RT at pH 6.5. The excess of linker was removed using desalting columns (Bio-Rad Econopac 10 DG) according to the instructions of the manufacturer and the linker-PSA conjugate was transferred into reaction buffer.

The MPBH-PSA conjugate was added to the oxidized rFVIII (0.105 mg/ml protein) and the reaction mixture was incubated for 2 h at RT under gentle shaking. The rFVIII-PSA conjugate was purified by HIC using a prepacked Butyl Sepharose column (GE Healthcare, Butyl HiTrap FF 5 ml). To allow hydrophobic interactions of the conjugate with Butyl Sepharose the sample was cooled to 2-8° C. and the ionic strength of the reaction mixture was increased to a conductivity of approx. 185 mS/cm by adding a buffer solution containing 5 M NaCl (50 mM Hepes, 5 M NaCl, 6.7 mM $CaCl_2$, 0.01% Tween, pH 6.9). The reaction mixture was loaded onto the column that was equilibrated with equilibration buffer pH 6.9 (containing 50 mM Hepes, 3 M NaCl, 6.7 mM $CaCl_2$, 0.01% Tween 80) with a flow rate of 1.2 cm/min. Unbound sample was washed out with 10 column volumes (CV) of equilibration buffer. The conjugate was eluted with a buffer of low ionic strength, pH 7.4 (50 mM Hepes, 6.7 mM $CaCl_2$) with a flow rate of 1.2 cm /min. During the chromatography process, samples and buffers were cooled using an ice bath. Finally, the pH of the eluate was adjusted to 6.9.

Example 13

Conjugation of rFVIII with Dextran

For conjugation of rFVIII with dextran, 2 ml rFVIII (638 mg, 3.4 mg/ml protein) were transferred to oxidation buffer (50 mM sodium acetate, pH 6) using desalting columns (Bio- Rad Econopac 10 DG) according to the manufacturer's instruction. The protein was then oxidated with 0.25mM $NaIO_4$ (1 h at 4° C. in the dark). The oxidated protein was first concentrated using vivaspin ultrafiltration spin columns (Sartorius Stedim Biotech GmbH) with a MWCO of 30 kDa according to the manufacturer's instructions. The sample was next dialyzed against reaction buffer (50 mM sodium phosphate pH 7) over night at 4° C.

After dialysis, 26.58 mg adipic acid dihydrazide (ADH) (Sigma) was added (500 fold molar excess) and the reaction mixture was incubated 2 h at RT at pH 7 under gentle shaking. ADH was removed using desalting columns (Bio-Rad Econopac 10 DG) according to the instructions of the manufacturer. Ten mg aldehyde-activated dextran (Pierce) was added (17 fold molar excess to protein) and the mixture was incubated for 2 h at RT, pH 7.

The conjugate was purified by IEX chromatography on Q-Sepharose HP (GE-Healthcare). The sample was loaded onto a column (6.4 mm×3 cm, V=1 ml) that was equilibrated with buffer A (50 mM sodium phosphate pH 6.8) with a flow rate of 0.5 ml/min. Unbound sample was washed out with 5 CV buffer A. Finally, the conjugate was eluted with a linear salt gradient (0-100% buffer B [50 mM sodium phosphate pH 6.8+1M NaCl] in 10 CV) with a flow rate of 0.5 ml/min.

The invention claimed is:

1. A method of treating a bleeding disorder comprising administering a composition to a subject in need thereof in an amount effective to treat said bleeding disorder, said composition comprising (i) a conjugate comprising a native Factor VIII modified with a water soluble polymer bound thereto, said water soluble polymer attached to the modified Factor VIII via an oxidized carbohydrate moiety, said modified Factor VIII retaining at least 50% of native FVIII activity, and (ii) a pharmaceutically acceptable excipient.

2. The method of claim 1, wherein said composition is substantially free from albumin.

3. The method of claim 1, wherein said water soluble polymer is attached to said oxidized carbohydrate moiety via a linker.

4. The method of claim 3, wherein said linker is 4-[4-N-maleimidophenyl]butyric acid hydrazide (MBPH).

5. The method of claim 3, wherein the linker is releasable or hydrolysable.

6. The method of claim 1, wherein said oxidized carbohydrate moiety is located in a native Factor VIII B domain.

7. The method of claim 1, wherein said water soluble polymer is selected from the group consisting of polyethylene glycol (PEG), polysialic acid (PSA) and dextran.

8. The method according to claim 1, wherein said modified Factor VIII retains at least 60% of native FVIII activity.

9. The method according to claim 8, wherein said modified Factor VIII retains at least 70% of native FVIII activity.

10. The method according to claim 1, wherein said bleeding disorder is hemophilia A.

11. The method of claim 1, wherein said water soluble polymer has a molecular weight of 2,000 to 150,000 Da.

12. The method of claim 11, wherein said water soluble polymer has a molecular weight of 5,000 to 50,000 Da.

13. The method of claim 1, wherein said water soluble polymer is branched.

14. The method of claim 1, wherein said water soluble polymer is linear.

15. The method of claim 1, wherein the Factor VIII is a recombinant Factor VIII.

16. The method of claim 1, wherein the Factor VIII is a plasmatic Factor VIII.

17. The method of claim 1, wherein the composition comprises a plurality of conjugates, each having at least one water soluble polymer bound to a native Factor VIII, said water soluble polymer attached to the modified Factor VIII via one or more oxidized carbohydrate moieties, said modified Factor VIII retaining at least 50% of native FVIII activity, and (ii) a pharmaceutically acceptable excipient.

18. The method of claim 1, further comprising an unconjugated Factor VIII moiety.

19. A kit comprising a pharmaceutical composition comprising (i) a conjugate comprising a native Factor VIII modified with a water soluble polymer bound thereto, said water soluble polymer attached to the modified Factor VIII via an oxidized carbohydrate moiety, said modified Factor VIII retaining at least 50% of native FVIII activity, and (ii) a pharmaceutically acceptable excipient; packaged in a container with a label that describes use of the pharmaceutical composition in the method of claim 1.

20. A kit according to claim 19, wherein the pharmaceutical composition is packaged in a unit dose form.

21. A kit comprising a first container comprising a conjugate comprising a native Factor VIII modified with a water soluble polymer bound thereto, said water soluble polymer attached to the modified Factor VIII via an oxidized carbohydrate moiety, said modified Factor VIII retaining at least 50% of native FVIII activity, and a second container comprising a physiologically acceptable reconstitution solution for said conjugate in the first container, wherein said kit is packaged with a label that describes use of the pharmaceutical composition in the method of claim 1.

22. A kit according to claim 21, wherein the pharmaceutical composition is packaged in a unit dose form.

* * * * *